United States Patent [19]

Yanaihara et al.

[11] 4,404,133
[45] Sep. 13, 1983

[54] PEPTIDES AND METHOD FOR SYNTHESIZING THE SAME

[75] Inventors: Noboru Yanaihara, Shizuoka; Koji Konno, Iwaki, both of Japan

[73] Assignee: Kureha Kagaku Kogyo Kabushiki Kaisha, Tokyo, Japan

[21] Appl. No.: 272,979

[22] Filed: Jun. 12, 1981

[30] Foreign Application Priority Data

Jun. 25, 1980 [JP] Japan ................................. 55-86952

[51] Int. Cl.³ ..................... C07C 103/52; G01N 33/00
[52] U.S. Cl. ............................... 260/112.5 R; 424/1.5
[58] Field of Search .................... 260/112.5 R; 424/1.5

[56] References Cited

U.S. PATENT DOCUMENTS

| | | | |
|---|---|---|---|
| 4,148,886 | 4/1979 | Bach et al. | 260/112.5 R |
| 4,207,311 | 6/1980 | Brown et al. | 260/112.5 R |
| 4,229,438 | 10/1980 | Fujino et al. | 260/112.5 R |
| 4,301,065 | 11/1981 | Bach et al. | 260/112.5 R |
| 4,331,646 | 5/1982 | Delaage | 260/112.5 R |

FOREIGN PATENT DOCUMENTS 2407471  5/29  France.
2014581  8/79  United Kingdom.

OTHER PUBLICATIONS

Nature, vol. 260 (1976) 713–715.
Journal of Biological Chemistry 252, (1977) 8045–8047.
Pleau el. al., Dosage Radioimmunologigue du Facteur Thymique Seoique (FTS) IAEA—SM220/68 pp. 505-510.

*Primary Examiner*—Delbert R. Phillips

[57] ABSTRACT

Disclosed herein are the peptides possibly radio-labelled and having primary structures represented by the general formula (I):

$$\text{X-Ser-Gln-Gly-Gly-Ser-Asn-Y} \quad \text{(I)}$$

wherein
(1) X is H-Tyr-Gln-Ala-Lys and Y is a hydroxyl group,
(2) X is pGlu-Ala-Lys(N$^\epsilon$-Tyr-H) and Y is a hydroxyl group, or
(3) X is pGlu-Ala-Lys and Y is Tyr-OH.

These peptides can be synthesized by bonding a predetermined amino acid or a peptide to the nitrogen at one of the two ends of the starting material, H-Asn-OH or H-Asn-Tyr-OH, while leaving the carboxyl group at the other end thereof in a free state, and by successively repeating the same procedure on the thus prepared peptides.

The symbols, Ser, Gln, Gly, Asn, Tyr, Ala and Lys used herein represent respectively a divalent residue formed by removing one hydrogen atom from the amino group of and further removing one hydroxyl group from the carboxyl group of the respective alpha-amino acids, serine, glutamine, glycine, asparagine, tyrosine, alanine and lysine. For instance, Ser represents the divalent residue, —NH—CH(CH$_2$OH)—CO—. The symbol, pGlu, represents a monovalent residue formed by removing one hydroxyl group from the carboxyl group of pyroglutamic acid.

6 Claims, No Drawings

PEPTIDES AND METHOD FOR SYNTHESIZING THE SAME

SUMMARY OF THE INVENTION

The present invention provides derivatives of tyrosine, which have physiological functions similar to those of so-called Serum Thymic Factor (hereinafter abbreviated as STF) and are easily labelled with radioactive iodine in the case when radioimmunoassay is carried out.

BACKGROUND OF THE INVENTION

As for the primary structure of STF, Jean-Fransois Bach et al. reported in 1977 that an active ingredient extracted from swine serum showing activities as STF had the following structure:

[refer to J. Biol. Chem., 252 8045(1977)].

The thymus is an organ having close relationships to antibody-production and cellular immunity, and it has been known that several peptides considered to be secreted from the thymus have actions of regulating the immunological functions. The action of STF on the thymic cells to increase the thymic cyclic-AMP resulting in contribution to the differentiation of thymic cells has been indicated by A. Astaldi et al. [refer to Nature (London), 260, 713(1977)], and thus STF is an interesting peptide as a factor secreted from the thymus and contained in the serum.

In the case where the immuno-regulating action of STF is utilized clinically or in other purposes, it is necessary to accurately catch the concentration of STF in blood, and that the concentration of STF in blood is in the order of several pg/ml has been reported by Jeanfransois Bach et al. (refer to Bullein de L'Insututut Pasteur, 1978, 325). Although it is effective to carry out radioimmunoassay (RIA) in analyzing such a substance of presence in a minute amount, as is seen its amino acid-composition, STF does not contain such an amino acid having aromatic ring(s) which is possibly labelled with radioactive iodine as in histidine. Accordingly, in order to carry out RIA, it is necessary to introduce a structure easily subjected to radio-labelling into the substance in advance of using such a substance to RIA. Moreover, although a plenty of pure STF and radiolabelled STF is necessary to carry out RIA of STF, it is not a profitable method to collect a plenty of STF from animal blood and in a pure form when the amount of presence of STF present in nature, the difficulty of purfying STF, etc. are considered.

Accordingly, the synthesis of easily radio-labellable derivatives of STF has been expected.

DETAILED DESCRIPTION OF THE INVENTION

The present inventors have been successful to synthesize derivatives of tyrosine of a similar chemical structure to STF, which are easily labelled with radioactive iodine, and those actually labelled with radioactive iodine. Besides, it has been found that the thus synthesized derivatives of tyrosine of a similar chemical structure to STF have fairly high physiological activities similar to those of STF and that the activities are equal to those of STF.

The derivatives of tyrosine, i.e., the peptides of the present invention have primary structures represented by the formula (I):

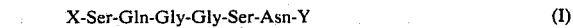

wherein

X represents H-Tyr-Gln-Ala-Lys, pGlu-Ala-Lys(N$^\epsilon$-Tyr-H) or pGlu-Ala-Lys, and Y represents OH when X represents H-Tyr-Gln-Ala-Lys or pGlu-Ala-Lys(N$^\epsilon$-Tyr-H) and Y represents Tyr-OH when X represents pGlu-Ala-Lys, -Lys(N$^\epsilon$-Tyr-H) indicating that the amino group at the $\epsilon$-position of the side chain of lysine is bonded to tyrosine with a peptide bonding.

Definite peptides of the present invention are:
Compound No.1: pGlu-Ala-Lys(N$^\epsilon$-Tyr-H)-Ser-Gln-Gly-Gly-Ser-Asn-OH,
Compound No.2: pGlu-Ala-Lys-Ser-Gln-Gly-Gly-Ser-Asn-Tyr-OH and
Compound No.3: H-Tyr-Gln-Ala-Lys-Ser-Gln-Gly-Gly-Ser-ASn-OH.

The characteristic feature of the present invention in carrying out the synthesis of the peptide of the present invention is the use of an amino acid or a peptide in which the carboxyl group at the C-end has not been protected by formation of ester group, etc. as in H-Asn-OH, H-Asn-Tyr-OH, H-Ser-Asn-OH or H-Ser-Asn-Tyr-OH. Because of the presence of the not-protected carboxyl group at the C-end by esterification, it is not necessary to carry out a treatment with acid or alkali to remove the protecting group after synthesis, and thus the hydrolysis of amide group in the side chain of glutamin and asparagin by the acid or alkali does not occur.

Accordingly, as a method of condensation in the synthesis, such a method in which the reaction proceeds without any problem even when a free carboxyl group of the reactants is present, as those, for instance, azide method, mixed acid anhydride method or active ester method, is preferably adopted.

On carrying out the above-mentioned condensation in the present invention, an amino acid or a peptide having its carboxyl group at the C-end not protected is used, however, it is necessary to protect the amino group at the N-end or in the side chain of the acid component. As the group for protecting the amino group, any protecting group utilized in ordinary peptide-synthesis for protecting amino groups can be used, for instance, benzyloxycarbonyl group, methoxybenzyloxycarbonyl group, chlorobenzyloxycarbonyl group, nitrobenzyloxycarbonyl group, phenylazobenzyloxycarbonyl group, methoxyphenylazobenzyloxycarbonyl group, t-butoxycarbonyl group, 1-(1-biphenylyl)-isopropoxycarbonyl group, 1-(1-isopropyl-2-methyl)-propoxycarbonyl group, formyl group, acetyl group, benzoyl group, phthalyl group, tosyl group and 2-nitrophenylsulphenyl group.

For removing the protecting group after synthesis of the object compound, an ordinary method can be used. For instance, benzyloxycarbonyl group is removed in a solution of methanol at an ordinary temperature under an ordinary pressure in the presence of Pd catalyst by catalytic hydrogenating decomposition with a preferable result because of the easy treatment after the removal of the protecting group. The intentional addition of an acidic substance in an equimolecular or more amount to the peptide in the solvent frequently promotes the reaction. As for removing methoxybenzyloxycarbonyl-, chlorobenzyloxycarbonyl-, phenylazobenzyloxycarbonyl- and methoxyphenylazobenzyloxycarbonyl groups, the similar procedure can be taken.

On the other hand, t-butoxycarbonyl group can be removed by an acidic reagent, for instance hydrogen chloride in acetic acid or in ethyl acetate and trifluoroacetic acid, etc. 1-(1-Biphenyl)-isopropoxycarbonyl-, 1-(1-isopropyl-2-methyl)propoxycarbonyl- and 2-nitrophenylsulphenyl groups are also removed by the similar reagent.

Since tosyl group is a relatively stable protecting group and cannot be removed by catalytic hydrogenating decomposition or acid-treatment, it is preferably removed by the treatment with metallic sodium in liquid ammonia.

As has been stated, the conditions for removing the protecting group are quite the same or quite different depending on the kinds of the protecting groups, and only the desired group is possibly removed while maintaining the other protecting group by suitably combining these conditions.

In the present invention, benzyloxycarbonyl-, t-butoxycarbonyl- and tosyl groups are the most conveniently utilizable groups for protection of amino group, and by using one of these groups, pure peptide can be synthesized in a favorable yield. The thus obtained peptide is purified by an ordinary procedure, for instance, recrystallization, extraction, chromatographical separation, etc.

The present inventors have purified the synthesized peptide by a combination of several procedures of purification until a single spot is obtained in the thin layer chromatogram by using a plurality of developing solvents, and have carried out identification of the product by amino acid analysis, infrared absorption spectroscopy, nuclear magnetic resonance spectroscopy, etc.

The peptides containing tyrosine synthesized and purified according to the present invention are novel peptides having physiological activities similar to those of STF, and since they are easily labelled with radioactive iodine, they are preferably effective as radiolabelled peptides in the case when RIA is carried out on STF.

Labelling the peptide with radioactive iodine can be accomplished by the conventional method.

The determination of STF-like activity of the tyrosine-containing peptide of the present invention was carried out by the Rosette test adopted by Jean-Fransois Bach et al. [refer to Journal Biol. Chem., 252, 8040(1977), and Japanese Patent Application Laying Open No. 16425/79, published on Feb. 7, 1979].

Some of the physical properties of the three peptides of the present invention are shown below:

(a) pGlu-Ala-Lys(N$^{\epsilon\text{-}Tyr\text{-}H}$)-Ser-Gln-Gly-Gly-Ser-Asn-OH (Compound No.1)

Peaks in thin layer chromatogram:
Rf$_1$ of 0.45; Rf$_2$ of 0.25 and Rf$_3$ of 0.54.
Specific rotatory power:
$[\alpha]_D^{24} = -49°(c=0.308$ in water)
Amino acid composition:
NH$_3$ of 2.05; Lys of 0.96; Tyr of 0.93; Ala of 0.98; Gly of 1.97; Glu of 2.04; Ser of 1.79 and Asp of 1.00.

(b) pGlu-Ala-Lys-Ser-Gln-Gly-Gly-Ser-Asn-Tyr-OH (Compound No.2)

Peaks in thin layer chromatogram:
Rf$_1$ of 0.41; Rf$_2$ of 0.12 and Rf$_3$ of 0.30.
Specific rotatory power:
$[\alpha]_D^{24} = -55.5°(c=0.263$ in water)
Amino acid composition:
NH$_3$ of 3.51; Lys of 1.04; Tyr of 0.89; Ala of 1.07; Gly of 2.06; Glu of 2.05; Ser of 1.90 and Asp of 1.00.

(c) H-Tyr-GLn-Ala-Lys-Ser-Gln-Gly-Gly-Ser-ASn-OH (Compound No.3)

Peaks in thin layer chromatogram:
Rf$_1$ of 0.29; Rf$_2$ of 0.10 and Rf$_3$ of 0.26.
Specific rotarory power:
$[\alpha]_D^{24} = -44.1°(c=0.279$ in water)
Amino acid composition:
NH$_3$ of 3.59; Lys of 1.06; Tyr of 0.92; Ala of 0.97; Gly of 1.97; Glu of 2.04; Ser of 1.82 and Asp of 1.00.

Notes:
(i) The developing solvents in thin layer chromatography were:
for Rf$_1$: a mixture of ethanol and aqueous 1 M CH$_3$COONH$_4$ solution of the ratio of 7:3.
for Rf$_2$: a 2:2:1 mixture of chloroform, methanol and concentrated aqueous ammoniacal solution.
for Rf$_3$: a 1:2:1 mixture of chloroform, methanol and concentrated aqueous ammoniacal solution.
(ii) The figures in amino acid composition show the relative mol ratio of each amino acid in the case when the molar amount of Asp is 1.00.

The synthetic examples, the examples of labelling the thus synthesized peptides with radioactive iodine and the examples of determination of physiological activities of the peptides are shown in detail as follows.

EXAMPLE 1

Synthesis of Compound No. 1

(1) Synthsis of H-Ser-Asn-OH

In 200 ml of dimethylformamide, 25.3 g of benzyloxycarbonylserine hydrazide was dispersed in suspension, and while keeping the suspension at $-35°$ to $-30°$ C., 50 ml of 6 N hydrogen chloride solution in dioxane was dropped into the suspension and then while keeping the suspension at $-30°$ to $-25°$ C., 15 ml of isoamyl nitrate was dropped into the suspension. After keeping the mixture for 5 min at $-20°$ to $-15°$ C., the mixture was cooled to $-35°$ to $-30°$ C., and 42 ml of triethylamine was dropped into the mixture. The thus obtained slurry-like material was added to a mixture composed of 15.0 g of asparagin hydrate, 50 ml of dimethylformamide, 200 ml of water and 28 ml of triethylamine, and the mixture was stirred for one hour at $-10°$ to $0°$ C. and then the stirring was continued for a night at room temperature. After drying the mixture at a reduced pressure almost to dryness, 100 ml of water was added to dissolve the semi-solid. After adjusting the pH of the aqueous solution to 7.0 by triethylamine, the solution was extracted with ethyl acetate, and the aqueous layer was adjusted to be 4.5 in pH with acetic acid and extracted with n-butanol. The substance obtained by evaporating n-butanol under a reduced pressure from the butanol-extract was dissolved into a solvent mixture of 150 ml of methanol, 150 ml of water and 5 ml of acetic acid, and the solution was subjected to catalytic hydrogenating decomposition at an ordinary temperature under an ordinary pressure in the presence of a catalyst of 3 g of 5% palladium on carbon for 5 hours. Then the reaction mixture was filtered, and the filtrate was condensed under a reduced pressure to obtain a product which was recrystallized from a mixture of water and ethanol in a yield of 45%.

The product, H-Ser-Asn-OH, melted at 155° to 157° C.

(2) Synthesis of H-Gly-Gly-Ser-Asn-OH

H-Ser-Asn-OH prepared in (1) and benzyloxycarbonyl-Gly-Gly-NHNH$_2$ were condensed according to the azide method, and the reaction mixture was extracted with n-butanol to separate benzyloxycarbonyl-Gly-Gly-Ser-Asn-OH as a product. The product was subjected to catalytic hydrogenating decomposition in the presence of 5% palladium on carbon to obtain H-Gly-Gly-Ser-Asn-OH melting at 219° C. with decomposition in a yield of 63%.

(3) Synthesis of H-Lys(N$^\epsilon$-tosyl)-Ser-Gln-Gly-Gly-Ser-Asn-OH

H-Gly-Gly-Ser-Asn-OH obtained in (2) and benzyloxycarbonyl-Lys(N$^\epsilon$-tosyl)-Ser-Gln-NH.NH$_2$ were condensed according to the azide method to obtain benzyloxycarbonyl-Lys(N$^\epsilon$-tosyl)-Ser-Gln-Gly-Gly-Ser-Asn-OH. It was subjected to catalytic hydrogenating decomposition in the presence of 5% palladium on carbon to obtain in object peptide, H-Lys(N$^\epsilon$-tosyl)-Ser-Gln-Gly-Gly-Ser-Asn-OH. After recrystallizing from a mixture of water and ethanol, the yield was 33%. The amino acid composition of the product was: NH$_3$ of 2.24; Lys of 0.28; Gly of 2.08; Glu of 0.99; Ser of 1.78 and Asp of 1.00.

(4) Synthesis of H-Ala-Lys(N$^\epsilon$-tosyl)-Ser-Gln-Gly-Gly-Ser-Asn-OH

In 30 ml of dimethylsulfoxide, 2.7 g of H-Lys(N$^\epsilon$-tosyl)-Ser-Gln-Gly-Gly-Ser-Asn-OH prepared in (3) was dissolved, and 0.5 ml of triethylamine was added to the solution. To the mixture, 20 ml of dimethylsulfoxide containing 1.56 g of benzyloxycarbonyl-alanine N-hydroxysuccinimide ester was added, and the mixture was stirred for a night at room temperature. Then, after evaporating the solvent from the reaction mixture under a reduced pressure, the residue was washed thoroughly with chloroform and dried. The dried residue was suspended in 100 ml of water and after adjusting the pH to 8.5 by adding triethylamine, the insoluble matter was removed by filtration. On bringing the filtrate to acidic with citric acid, a gel-like product was obtained. After filtering the gel-like product, washing the residue with ethanol and then ethyl acetate and drying the washed residue, the thus obtained benzyloxycarbonyl-Ala-Lys(N$^\epsilon$-tosyl)-Ser-Gln-Gly-Gly-Ser-Asn-OH was subjected to catalytic hydrogenating decomposition in the presence of 5% palladium on carbon to obtain the object peptide, H-Ala-Lys(N$^\epsilon$-tosyl)-Ser-Gln-Gly-Gly-Ser-Asn-OH. The crude product thus obtained was purified by Sephadex G-10 while using an aqueous 1 M acetic acid solution as an eluant. The amino acid composition of the thus purified product was: NH$_3$ of 2.10; Ala of 1.01; Lys of 0.35; Gly of 2.02; Glu of 0.99; Ser of 1.70 and Asp of 1.00.

(5) Synthesis of pGlu-Als-Lys-Ser-Gln-Gly-Gly-Ser-Asn-OH

Into a mixture of 25 ml of dimethylformamide and 15 ml of water, 0.9 g of H-Ala-Lys(N$^\epsilon$-tosyl)-Ser-Gln-Gly-Gly-Ser-Asn-OH obtained in (4) was dissolved, and after addition of 0.1 ml of triethylamine to the solution, benzyloxycarbonyl-pGlu N-hydroxysuccinimide ester was added to the solution, and the mixture was stirred for a night. Then the solvent was evaporated off from the reaction mixture and the residue was dissolved into water. After making the mixture acidic by citric acid, the thus formed gel-like product was collected by filtration and after washing the product with a dilute aqueous citric acid solution, water, ethanol and ethyl acetate in this order, the product was dried and then recrystallized from a mixture of dimethylformamide and ethanol. After subjecting the crystals to catalytic hydrogenating decomposition with 5% palladium on carbon, the product was dissolved in liquid ammonia and the protecting group of he product was removed by addition of metallic sodium. The thus treated product was subjected to an anion-exchange resin (IRA 411) and then purified by Biogel P-2 while using water as an eluant. The yield of purified object product was 42% and the amino acid composition was: NH$_3$ of 2.11; Ala of 0.99; Lys of 1.04; Gly of 2.03; Glu of 1.99; Ser of 1.78 and Asp of 1.00.

(6) The last step: Synthesis of Compound No. 1, pGlu-Ala-Lys(N$^\epsilon$-Tyr-H)-Ser-Gln-Gly-Gly-Ser-Asn-OH Into a mixture of 6 ml of dimethylformamide and 4 ml of water, 486 mg of pGlu-Ala-Lys-Ser-Gln-Gly-Gly-Ser-Asn-OH obtained in (5) was dissolved, and after addition of 0.14 ml of triethylamine to the solution, 10 ml of dimethylformamide containing 0.3 g of benzyloxycarbonyltyrosine N-hydroxysuccinimide ester was added to the mixture and the mixture was stirred for a night.

Then, after evaporating the solvent from the reaction mixture under a reduced pressure and adding a few drops of acetic acid to the residue, ether was added to deposite crystals. After washing the crystals with ethyl acetate, the crystals were dried and dissolved into aqueous 50% acetic acid and the solution was subjected to catalytic hydrogenating decomposition in the presence of 0.3 g of palladium black. After the reaction was over, the reaction mixture was filtered, and the filtrate was condensed under a reduced pressure. The residue was dissolved in 6 ml of water and the solution was subjected to chromatography on Biogel P-2 while using water as an eluant to purify the product. The yields of the object product was 35%, the amino acid composition of the product being:

NH$_3$ of 3.00; Ala of 0.98; Lys of 0.98; Gly of 2.00; Glu of 2.06; Ser of 1.89; Tyr of 1.02 and Asp of 1.00.

EXAMPLE 2

Synthesis of Compound No. 2

(1) Synthesis of H-Ser-Asn-Tyr-OH

Into 500 ml of dimethylformamide, 27.7 g of benzyloxycarbonyl-Asn-OH and 46.1 g of H-Tyr-O.benzyl.Tosyl-OH were dissolved, and into the thus formed solution, 18.6 g of N-hydroxy-5-norbonene-2,3-dicarboxyimide, 14.6 ml of triethylamine and 21.4 g of dicyclohexylcarbodiimide were added at −5° C., and the mixture was stirred for a night. After the reaction was over, the reaction mixture was filtered, and the filtrate was condensed under a reduced pressure to be a viscous liquid. On adding water to the viscous liquid, crystals deposited from the liquid. The crystals were washed with aqueous saturated solution of sodium hydrogen carbonate, dilute hydrochloric acid, ethanol and ether in this order and then dried. The thus obtained crystals were dissolved in a mixed solvent of 260 ml of dimethylformamide, 35 ml of water and 65 ml of acetic acid, and were subjected to catalytic hydrogenating decomposition in the presence of 1 g of palladium black at an ordinary temperature under an ordinary pressure for 7 hours.

Then, the reaction mixture was filtered, and the filtrate was condensed under a reduced pressure. Water was added to the condensate and the insoluble matter into water was filtered off, and the filtrate was condensed under a reduced pressure to obtain crystals, which were recrystallized from a mixture of water and ethanol to be H-Asn-Tyr-OH.CH$_3$COOH in a yield of 71%.

On the other hand, 9.12 g of benzyloxycarbonyl-Ser-NHNH$_2$ was suspended in 5.0 ml of dimethylformamide, and while cooling to −50° to −40° C., 18 ml of a 6 N hydrogen chloride solution in dioxane was added to the suspension, and then 5.4 ml of isoamyl nitrite was added to the mixture. After further adding 15.2 ml of triethylamine into the mixture, the thus prepared mixture was added to a mixed solvent of 36 ml of dimethylsulfoxide and 18 ml of dimethylformamide containing 10.9 ml of triethylamine and 11.0 g of the above-mentioned H-Asn-Tyr-OH.CH$_3$COOH and the reaction mixture was stirred for a night at the temperature of −5° to 0° C. Then, after evaporating the solvents from the reaction mixture under a reduced pressure, water was added to the mixture and the pH of the mixture was adjusted to 8 by sodium hydrogen carbonate. The thus adjusted mixture was extracted with ethyl acetate. On adding sodium chloride to the aqueous layer and acidifying the layer by citric acid, a gel-like substance was formed. The substance was collected by filtration, washed with water and dried to be 14.2 g of a dried substance. After dissolving the substance into a mixed solvent of 180 ml of methanol, 260 ml of water and 9 ml of acetic acid, the substance was subjected to catalytic hydrogenating decomposition in the presence of 0.5 g of palladium black at an ordinary temperature under an ordinary pressure. After the reaction was over, the reaction mixture was filtered, and the filtrate was condensed under a reduced pressure. On recrystallizing the residue from a mixture of water and ethanol, H-Ser-Asn-Tyr-OH was obtained in a yield of 62%. The product melted at a temperature higher than 200° C.

(2) Synthesis of H-Gly-Gly-Ser-Asn-Tyr-OH

H-Ser-Asn-Tyr-OH obtained as above was condensed with benzyloxycarbonyl-Gly-Gly-NHNH$_2$ according to the azide method to be benzyloxycarbonyl-Gly-Gly-Ser-Asn-Tyr-OH, and the product was subjected to catalytic hydrogenating decomposition in the presence of palladium black to obtain the object product, H-Gly-Gly-Ser-Asn-Tyr-OH.

(3) Synthesis of H-Lys(N$^\epsilon$-tosyl)-Ser-Gln-Gly-Gly-Ser-Asn-Tyr-OH

H-Gly-Gly-Ser-Asn-Tyr-OH obtained as above was condensed with benzyloxycarbonyl-Lys(N$^\epsilon$-tosyl)-Ser-Gln-NH.NH$_2$ by the azide method, and the condensate was subjected to catalytic hydrogenating decomposition in the presence of palladium black to be the object product in a yield of 42%. The amino acid composition of the product was: NH$_3$ of 2.19; Lys of 0.38; Gly of 2.00, Glu of 0.97, Ser of 1.81; Tyr of 0.99 and Asp of 1.00.

(4) Synthesis of H-Ala-Lys(N$^\epsilon$-tosyl)-Ser-Gln-Gly-Gly-Ser-Asn-Tyr-OH

Into a solution of 2.0 g of the above-mentioned H-Lys(N$^\epsilon$-tosyl)-Ser-Gln-Gly-Gly-Ser-Asn-Tyr-OH in 15 ml of dimethylsulfoxide, 0.22 ml of N-methylmorpholine was added. To the thus prepared mixture, a solution of 685 mg of benzyloxycarbonyl-ala N-hydroxysuccinimide ester in 5 ml of dimethylsulfoxide was added, and the mixture was stirred for a night at room temperature. The reaction mixture was then diluted with 200 ml of water and added with citric acid to form a gel-like precipitate, which was collected by filtration, washed with water, ethanol, ethyl acetate and ether in this order, dried and then recrystallized from a mixture of dimethylformamide and ethanol. After dissolving the crystals into aqueous 50% acetic acid solution, they were subjected to catalytic hydrogenating decomposition in the presence of palladium black. After filtration of the reaction mixture and evaporating the solvent from the filtrate, the thus separated substance was recrystallized from an aqueous ethanolic solution, washed with ethanol and ether and dried to be the object product in a yield of 64%. The thus obtained product showed the following amino acid composition:

NH$_3$ of 2.01; Ala of 1.05; Lys of 0.30; Gly of 2.08, Glu of 0.96; Ser of 1.71; Tyr of 0.94 and Asp of 1.00.

(5) The last step: Synthesis of pGlu-Ala-Lys-Ser-Gln-Gly-Gly-Ser-Asn-Tyr-OH

Into a solution of 950 mg of the above-mentioned H-Ala-Lys(N$^\epsilon$-tosyl)-Ser-Gln-Gly-Gly-Ser-Asn-Tyr-OH in 15 ml of dimethylsulfoxide, 0.1 ml of N-methylmorpholine and then 355 mg of benzyloxycarbonyl-pGlu N-hydroxysuccinimide ester were added, and the mixture was stirred for a night at room temperature. After the reaction was over, 300 ml of water was added to the reaction mixture and the mixture was made acidic with the addition of citric acid and cooled with water. The thus separated gel-like product was collected by filtration, washed with a dilute aqueous citric acid solution, water, ethanol, ethyl acetate and ether in this order and dried. The dried substance was subjected to catalytic hydrogenating decomposition in the presence of 10% palladium on carbon, and the hydrogenated material was dissolved in 200 ml of liquid ammonia. Metallic sodium was added to the solution little by little, and at the time point where the solution was tinged with blue, 1 g of ammonium chloride was added to the solution for neutralization. After evaporating ammonia, the residue was dissolved in 8 ml of water and extracted with ether. The aqueous layer was separated and subjected to the treatment of Biogel P-2 for purification while using water as an eluant. The purified product obtained in a yield of 46% showed the following amino acid composition: NH$_3$ of 3.51; Ala of 1.07; Lys of 1.04; Gly of 2.06; Glu of 2.05; Ser of 1.90; Tyr of 0.98 and 1.00 of Asp.

EXAMPLE 3

Synthesis of Compound No. 3

(1) Synthesis of
H-Tyr-Gln-Ala-Lys-Ser-Gln-Gly-Gly-Ser-Asn-OH

Into a solution of 1.006 g of benzyloxycarbonyl-Tyr-Gln hydrazide in 40 ml of dimethylformamide, while cooling, 1.1 ml of a 6 N solution of hydrogen chloride in dioxane was dropped, and then, 0.4 ml of isoamyl nitrite and 0.93 ml of triethylamine were added to the mixture. Into the thus prepared mixture, a solution of 1.696 g of H-Ala-Lys(N$^\epsilon$-t-butoxycarbonyl)-Ser-Gln-Gly-Gly-Ser-Asn-OH in a mixed solvent of 20 ml of dimethylformamide and 20 ml of water and 0.28 ml of triethylamine was added, and the mixture was stirred for one hour at −15° C. and then for 3 days at 0° to 4° C. After the reaction was over, the solvents were evaporated from the reaction mixture under a reduced pressure, and the residue was dissolved in water containing a few drops of acetic acid. After again evaporating the solvent under a reduced pressure, ether was added to the residue to separate crystals, which were washed with ethyl acetate, dried and recrystallized from a mixed solvent of dimethylformamide and ethanol. After subjecting the crystals to catalytic hydrogenating decomposition in the presence of palladium black, the hydrogenated material was dissolved in 10 ml of trifluoroacetic acid containing 1 ml of anisol, and the solution was stirred for one hour at room temperature.

After evaporating the solvent from the solution, ether was added to the residue to separate crystals, which were washed with ether and dried. The crystals were dissolved in water and after passing the solution through a column of anion-exchange resin (IRA-411), the solution was purified by Biogel P-2 while using water as an eluant. The thus prepared object compound showed the following amino acid composition: $NH_3$ of 3.15; Ala of 1.01; Lys of 1.01; Gly of 1.98; Glu of 2.02, Ser of 1.80; Tyr of 1.00 and Asp of 1.00.

EXAMPLE 4

Rosette Test

A mouse after 10 weeks of its birth was subjected to extirpation of its thymus, and after 10 days of extirpation, when the splenic cells of the mouse were still in not-differentiated state and had few theta-antigen on these surface otherwise induced by the influence of the serum thymic factor, the spleen of the mouse was extirpated.

The cells of the thus extirpated spleen were subjected to the following tests to see the formation of "rosette" under a microscope:

(1) Test No. 1:

The splenic cells were incubated with sheep red blood cells in the presence of azathiopurine at a concentration of 10 micrograms/ml. The number of rosette-like aggregates formed by the combination of T-cell among the splenic cells and sheep red blood cells was countered unter a microscope. The number of the rosette-like aggregate (so-called "rosette" in this type of experiments) was, on the average, 10/ml.

(2) Test No. 2:

The splenic cells were incubated with sheep red blood cells in the presence of azathiopurine at the same concentration as in (1) and further in the presence of each of the respective synthesized peptides in Examples 1 to 3 and a specimen of STF collected from an adult mouse. The formation of "rosette" in each incubate was observed as in (1) under a microscope, the number of "rosette" being, on the average, 4.2; 4.0; 3.5 and 5.0, respectively.

(3) Evaluation of rate of inhibiting rosette-formation:

In the absence of STF, the splenic cells of the adult thymectomized mice form "rosettes" by combining with sheep red blood cells (more than two red blood cells combining with one splenic cell) regardless of the presence and absence of azathiopurine at the concentration as in (1) when incubated with sheep red blood cells.

However, in the presence of STF or a substance with STF-like activity, the theta-antigen is induced on the cell surface of T-cells, and as a result, azathiopurine inhibits the formation of "rosette" between sheep red blood cells and the splenic cells having the theta-antigen on its surface at the same concentration as in (1) or (2).

Thus, the activity of STF or a substance having STF-like activity in preventing the formation of "rosette" is represented and calculated by the following formula:

$$\text{Activity} = \frac{N_o - N_i}{N_o} \times 100$$

wherein $N_o$ means the number of rosettes formed in the case where no STF nor a substance having STF-like activity was present and azathiopurine was present, and $N_i$ means the number of rosettes formed in the cases where
(1) STF and azathiopurine were present and
(2) a substance having STF-like activity and azathiopurine were present, respectively.

Using the date obtained in Test No. 2 in the above-mentioned formula, the activity of the specimen of STF, and the activities of the peptides synthesized in Examples according to the present invention were obtained, the activities being:

| Substance | Activity of preventing "rosette" formation |
|---|---|
| STF | 50% |
| Compound No. 1 | 58% |
| Compound No. 2 | 60% |
| Compound No. 3 | 65% |

EXAMPLE 5

Radio-labelling of the synthesized peptide

Into 20 microliters of aqueous 1.0 M phosphate buffer solution of pH of 7.3, 10 microliters of aqueous 0.1 M acetic acid solution containing 5 micrograms of Compound No. 3 of the present invention, H-Tyr-Gln-Ala-Lys-Ser-Gln-Gly-Gly-Ser-Asn-OH, 10 microliters of water containing 1 mCi of sodium 125 iodide and 20 micrograms of chloramin T were added in the above-mentioned order.

After shaking the mixture for 20 sec, 50 microliters of water containing 100 micrograms of sodium hydrogen metasulfite and 10 microliters of aqueous 10% potassium iodide solution were added to the mixture.

The thus formed mixture was subjected to gell chromatography while using Sephadex G-10 as a column material and aqueous 0.1 M acetic acid solution as an eluant to purify the product. The weight of the thus obtained labelled product was 4.0 microgram containing 46% of the radioactive iodine in sodium iodide used in labelling. The specific radioactivity of the thus labelled peptide, Compound No. 3 of the present invention, due to $^{125}I$, was 115 mCi/mg.

What is claimed is:

1. A peptide with a primary structure represented by the general formula (I):

X-Ser-Gln-Gly-Gly-Ser-Asn-Y wherein
(1) X represents H-Tyr-Gln-Ala-Lys and Y represents a hydroxyl group,
(2) X represents pGlu-Ala-Lys($N^\epsilon$-Tyr-H) and Y represents a hydroxyl group, or
(3) X represents pGlu-Ala-Lys and Y represents a Tyr-OH group. with the proviso that (a) —Lys($N^\epsilon$-Tyr-H) means that the amino group at the $\epsilon$-position of the side chain of lysine has been bonded to tyrosine via a peptide bonding, and (b) pGln means a group formed by removing a hydroxy group of the carboxy group of pyroglutamic acid.

2. The peptide according to claim 1, pGlu-Ala-Lys($N^\epsilon$-Tyr-H)-Ser-Gln-Gly-Gly-Ser-Asn-OH.

3. The peptide according to claim 1, pGlu-Ala-Lys-Ser-Gln-Gly-Gly-Ser-Asn-Tyr-OH.

4. The peptide according to claim 1, H-Tyr-Gln-Ala-Lys-Ser-Gln-Gly-Gly-Ser-Asn-OH.

5. The peptide according to claim 1 labelled with radioactive iodine.

6. The peptide according to claims 2, 3 or 4 labelled with radioactive iodine.

* * * * *